(12) United States Patent
Cigaina

(10) Patent No.: US 6,908,487 B2
(45) Date of Patent: Jun. 21, 2005

(54) ANTI-GASTROESOPHAGEAL REFLUX VALVULAR PROSTHESIS

(75) Inventor: Valerio Cigaina, Villorba (IT)

(73) Assignee: Transneuronix, Inc., Mt. Arlington, NJ (US)

( * ) Notice: Subject to any disclaimer, the term of this patent is extended or adjusted under 35 U.S.C. 154(b) by 222 days.

(21) Appl. No.: 10/259,263

(22) Filed: Sep. 27, 2002

(65) Prior Publication Data

US 2003/0078615 A1 Apr. 24, 2003

(30) Foreign Application Priority Data

Oct. 3, 2001 (IT) .................................... MI2001A2046

(51) Int. Cl.$^7$ ............................................... A61F 2/04
(52) U.S. Cl. .............................. 623/23.67; 623/23.65; 606/202; 600/37
(58) Field of Search .................... 607/40; 606/202; 623/23.65, 23.67, 23.64, 23.68; 600/37

(56) References Cited

U.S. PATENT DOCUMENTS

| | | | | | |
|---|---|---|---|---|---|
| 1,679,978 A | * | 8/1928 | Konwiser et al. | ........... | 606/202 |
| 3,875,928 A | * | 4/1975 | Angelchik | .................... | 600/37 |
| 4,465,076 A | * | 8/1984 | Sturgeon | ..................... | 600/499 |
| 5,006,106 A | * | 4/1991 | Angelchik | .................... | 600/37 |
| 5,316,543 A | * | 5/1994 | Eberbach | ..................... | 600/37 |
| 5,690,691 A | * | 11/1997 | Chen et al. | .................... | 607/40 |
| 5,919,233 A | * | 7/1999 | Knopf et al. | ............... | 128/898 |
| 6,097,984 A | * | 8/2000 | Douglas | ...................... | 607/40 |
| 6,432,040 B1 | * | 8/2002 | Meah | ........................... | 600/37 |
| 6,463,935 B1 | * | 10/2002 | Forsell | ....................... | 128/899 |
| 2001/0011543 A1 | * | 8/2001 | Forsell | ....................... | 128/899 |

FOREIGN PATENT DOCUMENTS

| EP | 0 485 047 | 5/1992 |
|---|---|---|
| EP | 0 628 292 | 12/1994 |
| EP | 1 004 330 | 5/2000 |

* cited by examiner

*Primary Examiner*—Paul B. Prebilic
(74) *Attorney, Agent, or Firm*—Fitch, Even, Tabin & Flannery

(57) ABSTRACT

The anti-gastroesophageal reflux valvular prosthesis has a body presenting a seat of substantially semicircular shape engageable with the gastric wall of the stomach connected to the body through connectors and inflatable for the variation of this volume to accentuate the angle of His (cardiac incisure) and to improve the natural valvular anti-reflux system.

6 Claims, 2 Drawing Sheets

ANTI-GASTROESOPHAGEAL REFLUX VALVULAR PROSTHESIS

FIELD OF THE INVENTION

The present invention relates to an anti-gastroesophageal reflux valvular prosthesis.

BACKGROUND OF THE INVENTION

As is known, the term "hiatal hernia" is used to define a dislocation of an abdominal viscus of the thorax through an aperture in the diaphragm called the hiatoesophageal orifice, normally traversed by the esophagus.

Through this aperture in the diaphragm the esophagus can abnormally reascend the thorax, determining a sliding (rotational) hernia along with a portion (generally the most proximal portion) of the stomach (cardia).

The sliding hernia is generally associated with a reflux pathology, that is esophagitis.

When the border between esophagus and stomach shifts within the territory of the thorax, where the pressures are opposite the abdominal pressures (during inspiration, in the thorax there are negative values and positive ones in the abdomen), the acid content of the stomach lingers a little too long in the last tract of the esophagus and tries to digest the mucosa.

Eleven percent of the population experiences symptomatic gastroesophageal reflux on a daily basis.

When gastroesophageal reflux is symptomatic, a pathological entity is always present as a consequence of the reflux, for example esophagitis.

Recent studies suggest that the increase of esophageal cancer in industrial society may be linked precisely to the columnar transformation of the distal esophageal mucosa as a consequence of chronic reflux.

To avoid at least somewhat the drawbacks complained of above, medical reflux therapy based on pro-kinetic and antacid agents is applied.

However, when the aforesaid therapy also fails, surgical intervention is provided, resulting in such anatomical changes as to allow the possible hiatal hernia to be corrected and the anti-reflux mechanism to be improved.

Nevertheless, the great disadvantage of surgical intervention is that it frequently leads to complications and disorders that are sometimes difficult for the patient to tolerate.

OBJECTS OF THE INVENTION

The object of the present invention is to eliminate the drawbacks of the known technique described above.

An important object of the invention is to provide an anti-reflux gastroesophageal valvular prosthesis that helps avoid surgical intervention that could make anatomical changes and, consequently, surgical overcorrection that would lead to complications and disorders that the patient cannot tolerate.

Another object of the invention is to provide a valvular prosthesis that makes it possible to keep the last tract of esophagus in the abdomen by closing the diaphragmatic passage at the same time, surpassing medical reflux therapy and surgical interventions liable to bringing about anatomical changes that the patient cannot tolerate.

It is also an object of the invention is to provide a prosthesis that acts in a substantially natural manner, so that the more the stomach dilates proximally due to the presence of food and the more the angulation is automatically accentuated, the more the cardiac esophagus and the stomach closes.

A further object of the invention is to provide a prosthesis that allows coupling with a gastric pacemaker to stimulate the gastric portion of the sphincteral smooth musculature, for example during nightly rest.

It is also an object of the invention to provide a prosthesis that can be inserted into the abdomen with a laparoscopic or micro invasive technique and that can be removed without a new surgical intervention.

SUMMARY OF THE INVENTION

These objects are achieved with an anti-reflux gastroesophageal valvular prosthesis which comprises a body presenting a seat of substantially semicircular shape, engageable with the gastric wall of the stomach by connectors, and means for inflating at least the body for the variation of its volume to accentuate the angle of His and improve the natural anti-reflux valvular system.

BRIEF DESCRIPTION OF THE DRAWINGS

Additional characteristics and advantages of the invention will become apparent from the following description of a preferred, but not exclusive, embodiment of the valvular prosthesis according to the invention, illustrated in the attached drawing, in which.

SPECIFIC DESCRIPTION

Figure 1:
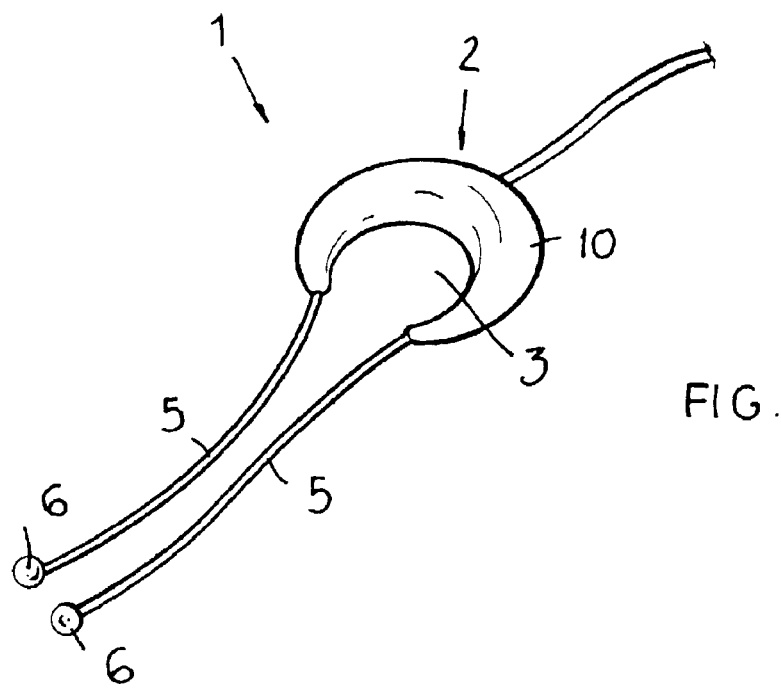
FIG. 1 is a schematic perspective view of the prosthesis according to the invention.
Figure 2:
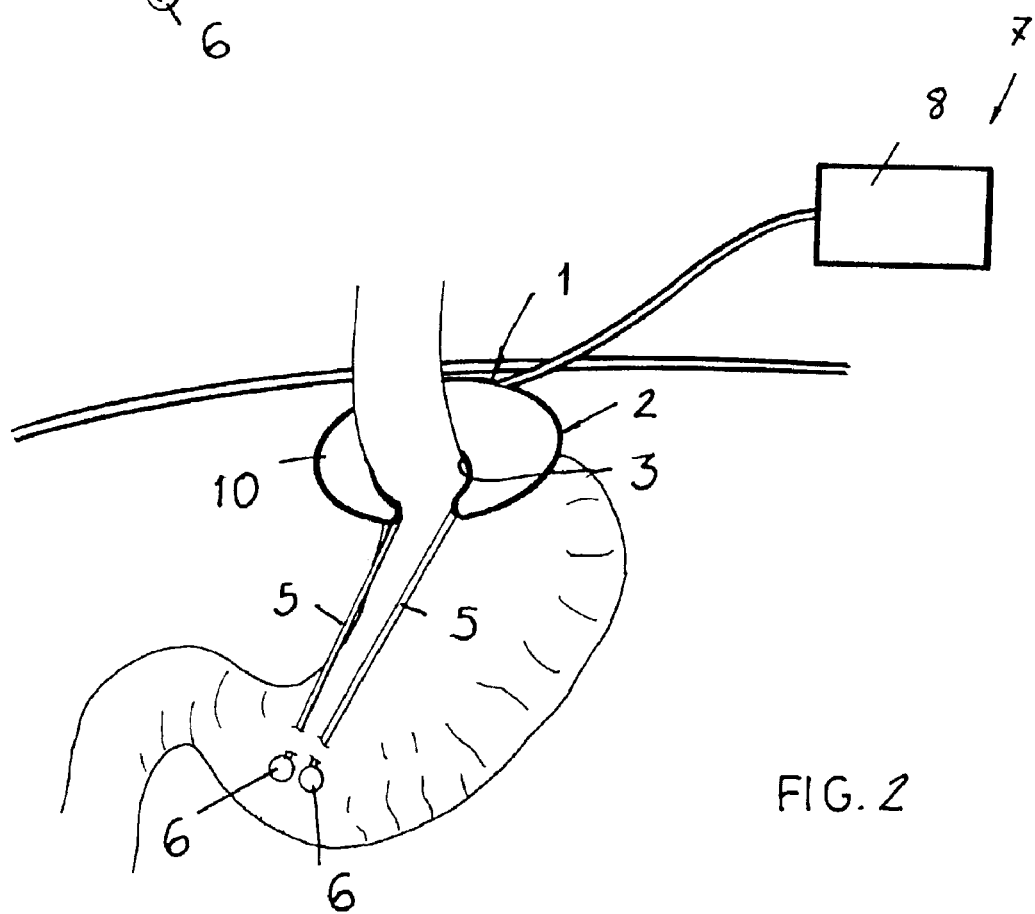
FIG. 2 is a schematic perspective view of the application of the prosthesis applied in the abdomen by a microinvasive laparoscopic technique according to the invention.
Figure 3:
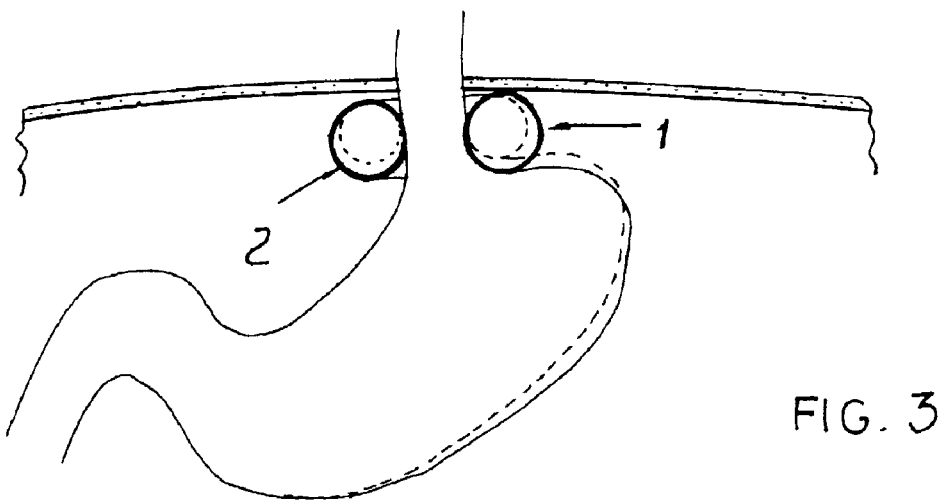
FIGS. 3 and 4 are diagrams which show the functioning of the prosthesis according to the invention.
Figure 4:
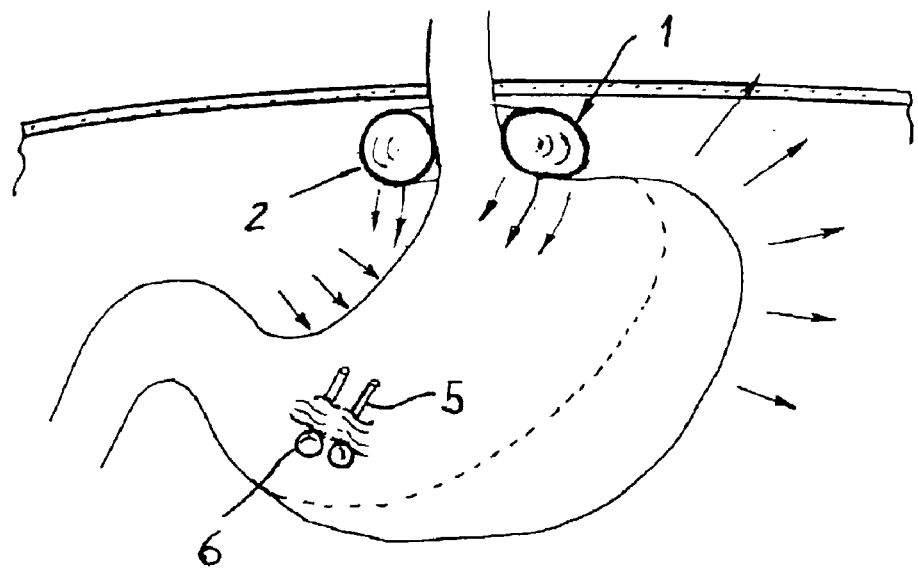

The anti-reflux gastroesophageal valvular prosthesis 1 comprises a body 2 having a seat 3 of a substantially semicircular shape.

Body 2 is of a substantially "half-moon" shape, defining a kind of collar that can be positioned inside the abdomen, in the zone of passage between esophagus and stomach, that is, in the gastroesophageal joint around the esophagus.

In particular, the prosthesis in inserted into the abdomen with a microinvasive laparoscopic technique.

The prosthesis further comprises means for engagement with the gastric wall of the stomach in the form of small tubes 5 which are connected to the body 2.

The prosthesis further comprises means of inflation capable of inflating at least body 2 to allow its volume to vary so as to accentuate the angle of His, that is, to accentuate the angulation between the esophagus and the stomach supported by the diaphragmatic cruses and simultaneously to improve the natural anti-reflux valvular system.

More precisely, the tubes 5 end in at least two distal inflatable elements, 6.

Small tubes 5 fluid-dynamically connect inflatable distal elements 6 to body 2 and are made of material that is elastically pliable axially, so as to vary their length elastically.

The means for inflation 7 can comprise a container 8 of a fluid for simultaneous inflation of both body 2 and distal elements 6.

Advantageously, inflatable elements 6 are anchored in the distal antrum, substantially side by side, (FIG. 7) and at a distance from body 2 substantially equal to the length of the small tubes 5.

Thus, as body 2 and, consequently, distal elements 6 inflate, there is, also thanks to the axial elasticity of small tubes 5, a restriction of the gastroesophageal tract and an improvement of continence with the simultaneous impediment of reflux.

In other words, the inflation of body 2 pulls the stomach partially herniated into the thorax downward, that is, toward the abdomen.

Thus the angle of His is accentuated and the natural anti-reflux valvular system is improved.

Furthermore, when the stomach distends due to the effect of the food accumulated inside it during the gastric phase of digestion, this angling is accentuated as the download stretching of the entire esophageal-gastric joint.

The body 2 and also the small tubes 5 and distal elements 6, may present a reinforcement core capable of resisting tractive forces to allow their removal without a new surgical intervention.

Moreover, the prosthesis described above may be easily coupled to the positioning of a gastric pacemaker and may be useful to stimulate the gastric portion of the sphincteral smooth musculature (inferior esophageal sphincter) perhaps during the patient's reflux timing.

Moreover, advantageously, body 2 present a median zone 10 of greater breadth suitable in shape and size for exerting pressure on the stomach only in the functional sense, mainly when the stomach is full of food, so that the distal elements and body 2 are automatically activated according to the natural functions during the patient's digestive phase.

Thus problems of decubitus are avoided, since the prosthesis always remains mobile, constricting the esophagus and lowering the stomach only in the functional sense and only when it is useful, that is, when the stomach is full of food that should not reascend into the esophagus.

The functioning of the prosthesis according to the invention appears evident from what has just been described and illustrated.

In practice it has been confirmed that the prosthesis of the invention is particularly advantageous for compensating remarkably both for the defects and inadequacies of medical reflux therapy based on pro-kinetic and antacid agents, and for the problems and drawbacks determined by surgical intervention that, in most cases, lead to anatomical changes with consequent complications and disturbances that the patient cannot tolerate.

Substantially, after suitable inflation, the prosthesis adjusts automatically and present an automatic reaction to the difficulties caused by esophagitis, in that the more the stomach dilates proximally due to the presence of food and the more the angulation is accentuated, the more the cardiac esophagus, that is, passageway between the esophagus and stomach closes.

The invention thus conceived is susceptible to numerous modifications and variations, all falling within the scope of the inventive concept, and furthermore, all details can be substituted by technically equivalent elements.

In practice any materials and dimensions may be used, depending on the demands and on the state of the art.

What is claimed is:

1. Anti-gastroesophageal reflux valvular prosthesis characterizing:

an inflatable body of substantially semicircular shape adapted to fit around the esophagus at a junction thereof with the stomach;

a pair of tubular connectors communicating with and extending from said body and adapted to pass through a stomach wall;

respective distal inflatable elements on said connectors and communicating therewith for anchoring to said wall upon inflation; and a source of an inflating fluid connected to said body for inflating said body to vary the volume thereof and adjust the angle of His of a patient and improve natural valvular antiflux action between the stomach and the esophagus and for inflating said distal elements through said connectors.

2. The prosthesis defined in claim 1 wherein said connectors are tubes composed of a material which is axially elastically pliable.

3. The prosthesis defined in claim 2 wherein said source is a container of a fluid for the simultaneous inflation of said body and said distal elements.

4. The prosthesis defined in claim 3 wherein said distal elements and said connectors are dimensioned and positioned to enable said inflatable elements to be anchored in the distal antrum of the stomach.

5. The prosthesis defined in claim 4 wherein said body has a reinforcement core resistant to tractive forces.

6. The prosthesis defined in claim 5 wherein said body and said distal elements are dimensioned and constructed and arranged for insertion and removal by laparoscopy.

* * * * *